United States Patent
Mezhinsky

(10) Patent No.: US 7,626,132 B2
(45) Date of Patent: Dec. 1, 2009

(54) FOOT CONTROLLER

(75) Inventor: Victor B. Mezhinsky, Brea, CA (US)

(73) Assignee: Alcon, Inc., Hunenberg (CH)

( * ) Notice: Subject to any disclaimer, the term of this patent is extended or adjusted under 35 U.S.C. 154(b) by 324 days.

(21) Appl. No.: 11/250,093

(22) Filed: Oct. 13, 2005

(65) Prior Publication Data

US 2007/0152508 A1 Jul. 5, 2007

(51) Int. Cl.
 *H01H 3/14* (2006.01)
(52) U.S. Cl. .................. 200/86.5; 606/166; 606/32; 307/119; 74/512
(58) Field of Classification Search ................ 200/86.5; 606/32, 41–42, 166, 167; 74/512, 560, 562; 307/119
See application file for complete search history.

(56) References Cited

U.S. PATENT DOCUMENTS

| | | | |
|---|---|---|---|
| 3,930,431 A | 1/1976 | Magadini | |
| 4,267,414 A | 5/1981 | Brueggeman | |
| 4,383,167 A | 5/1983 | Gmeinder et al. | |
| 4,652,215 A | 3/1987 | Kuroyanagi et al. | |
| 4,837,857 A | 6/1989 | Scheller et al. | |
| 4,901,454 A | 2/1990 | Walkhoff | |
| 4,965,417 A | 10/1990 | Massie | |
| 4,983,901 A | 1/1991 | Lehmer | |
| 5,091,656 A | 2/1992 | Gahn | |
| 5,268,624 A | 12/1993 | Zanger | |
| 5,422,521 A * | 6/1995 | Neer et al. | 307/119 |
| 5,554,894 A * | 9/1996 | Sepielli | 307/119 |
| 5,580,347 A | 12/1996 | Reimels | |
| 5,635,777 A | 6/1997 | Telymonde et al. | |
| 5,787,760 A | 8/1998 | Thorlakson | |
| 5,807,077 A * | 9/1998 | Lamanna | 417/234 |
| 5,910,110 A | 6/1999 | Bastable | |
| 5,983,749 A | 11/1999 | Holtorf | |
| 5,990,400 A | 11/1999 | Hoshino | |
| 6,010,496 A | 1/2000 | Appelbaum et al. | |
| 6,150,623 A * | 11/2000 | Chen | 200/86.5 |
| 6,179,829 B1 | 1/2001 | Bisch et al. | |
| 6,360,630 B2 | 3/2002 | Holtorf | |
| 6,452,120 B1 | 9/2002 | Chen | |
| 6,452,123 B1 * | 9/2002 | Chen | 200/86.5 |
| 6,514,268 B2 | 2/2003 | Finlay et al. | |
| D478,323 S | 8/2003 | Peterson et al. | |
| 6,639,332 B2 | 10/2003 | Metzler et al. | |
| 6,659,998 B2 | 12/2003 | DeHoogh et al. | |
| 6,674,030 B2 | 1/2004 | Chen et al. | |
| 6,743,245 B2 | 6/2004 | Lobdell | |
| 6,862,951 B2 | 3/2005 | Peterson et al | |
| 2003/0047434 A1 | 3/2003 | Hanson et al. | |
| 2003/0073980 A1 | 4/2003 | Finlay et al. | |
| 2003/0213333 A1 | 11/2003 | McVicar | |
| 2004/0106915 A1 | 6/2004 | Thoe | |

FOREIGN PATENT DOCUMENTS

EP    1 394 828 A1    3/2004

(Continued)

*Primary Examiner*—Kyung Lee
(74) *Attorney, Agent, or Firm*—W. David Lee

(57) ABSTRACT

A foot controller for a microsurgical system that includes a body, a switch disposed on the body, and a switch guard coupled to the body and disposed in a spaced relationship to an outer surface of the switch.

6 Claims, 1 Drawing Sheet

FOREIGN PATENT DOCUMENTS

| | | |
|---|---|---|
| GB | 1063067 | 3/1967 |
| WO | WO 96/13845 | 5/1996 |
| WO | WO 98/08442 | 3/1998 |
| WO | WO 99/14648 | 3/1999 |
| WO | WO 00/12037 | 3/2000 |
| WO | WO 02/01310 | 1/2002 |
| WO | WO 03/053293 A2 | 7/2003 |
| WO | WO 03/053293 A3 | 7/2003 |
| WO | WO 03/053294 A2 | 7/2003 |
| WO | WO 03/053294 A3 | 7/2003 |

\* cited by examiner

US 7,626,132 B2

FOOT CONTROLLER

FIELD OF THE INVENTION

The present invention generally pertains to microsurgical systems. More particularly, but not by way of limitation, the present invention pertains to foot controllers for the operation of such systems.

DESCRIPTION OF THE RELATED ART

Various foot controllers are used to control microsurgical systems, and particularly ophthalmic microsurgical systems. During ophthalmic surgery, a surgeon views the patient's eye through an operating microscope. To control the microsurgical system and its associated handpieces during the various portions of the surgical procedure, the surgeon must either instruct a nurse how to alter the machine settings on the surgical system, or use the foot controller to change such settings. Where possible, many surgeons prefer to use the foot controller to alter the machine settings on the surgical system, eliminating the need to converse with a nurse during the surgical procedure.

Many conventional foot controllers have a foot pedal that provides linear control of the functions of the surgical system or an associated handpiece, and a series of switches or buttons that provide binary control of such functions. Exemplary foot controllers for ophthalmic microsurgical systems are disclosed in International Publication Numbers WO 00/12037, WO 99/14648, WO 98/08442, WO 96/13845, and WO 02/01310 and U.S. Pat. Nos. 4,837,857; 4,965,417; 4,983,901; 5,091,056; 5,268,624; 5,554,894; 5,580,347; 5,635,777; 5,787,760; 5,983,749; 6,179,829; 6,639,332; and 6,659,998, all of which are incorporated herein by reference.

However, proper actuation of the pedals, buttons, and switches of conventional foot controllers can still be frustrated by certain operating room conditions, such as obstructions on or near the operating room floor like the leg of a stool or gurney or a vertical wall portion of a piece of furniture or equipment. Therefore, a need remains for an improved foot controller.

SUMMARY OF THE INVENTION

The present invention is an improved foot controller for a microsurgical system. In one aspect, the foot controller includes a body, a switch disposed on the body, and a switch guard coupled to the body and disposed in a spaced relationship to an outer surface of the switch. The switch is capable of being actuated by a side of a user's foot in a generally horizontal direction away from the body. The switch guard insures that the switch may be fully actuated in the generally horizontal direction.

BRIEF DESCRIPTION OF THE DRAWINGS

For a more complete understanding of the present invention, and for further objects and advantages thereof, reference is made to the following description taken in conjunction with the accompanying drawing, in which.

DETAILED DESCRIPTION OF THE PREFERRED EMBODIMENTS

Figure 1:
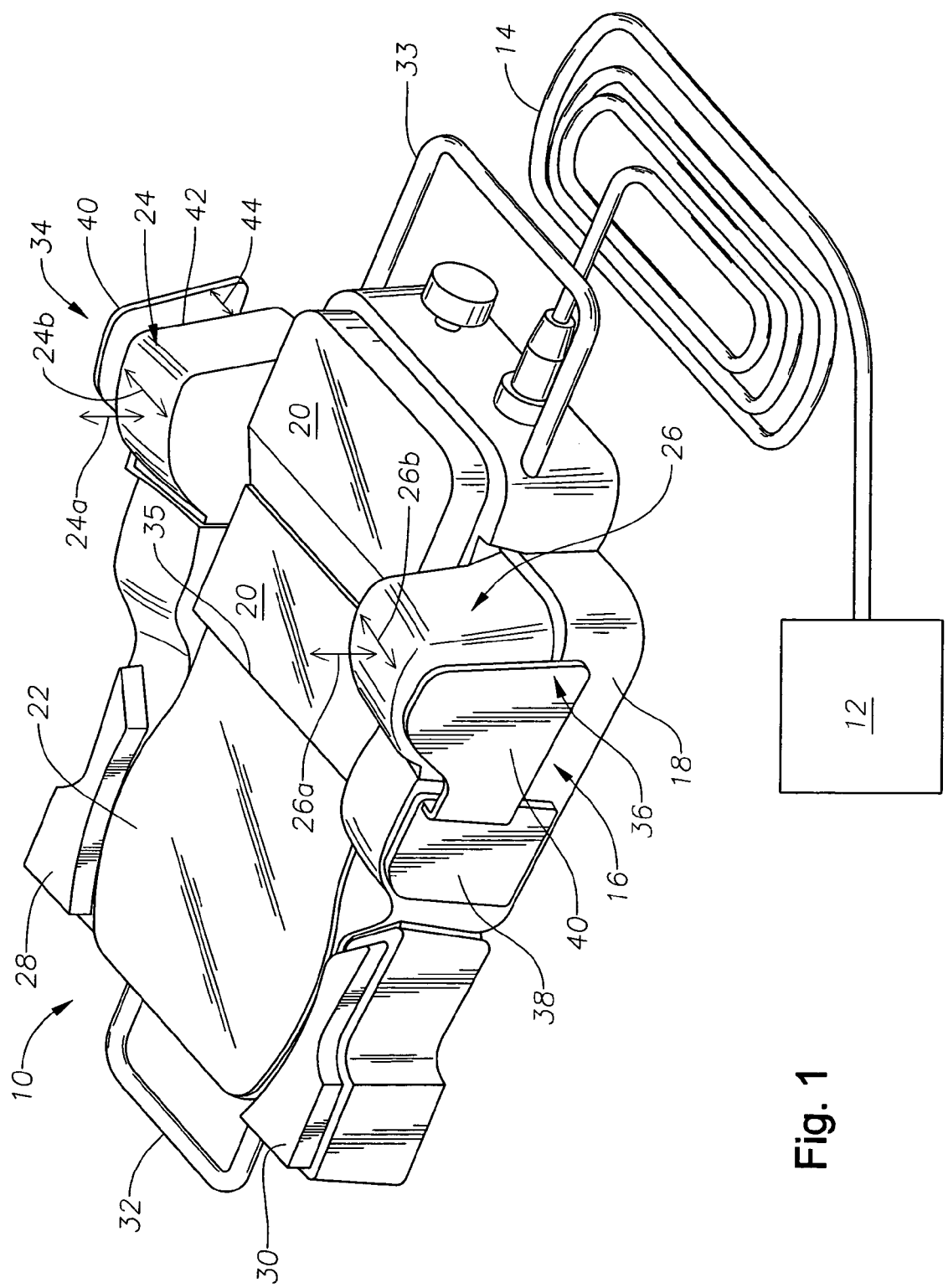
FIG. 1 is a top perspective view of a foot controller of a microsurgical system according to a preferred embodiment of the present invention.

The preferred embodiment of the present invention and its advantages are best understood by referring to FIG. 1 of the drawings, which shows a foot controller 10 electrically coupled to a microsurgical system 12 via an interface 14. Microsurgical system 12 is preferably an ophthalmic microsurgical system but may alternatively be any microsurgical system, including a system for performing optic, nasal, throat, or other surgeries. Interface 14 is preferably a cable but may alternatively be any conventional electrical interface.

Foot controller 10 preferably includes a body 16 with a base 18 that supports foot controller 10 on the operating room floor. Body 16 preferably includes a foot pedal 20, a heel rest 22, a left toe switch 24, a right toe switch 26, a left heel switch 28, a right heel switch 30, and handles 32 and 33.

Foot pedal 20 is preferably rotationally coupled to body 16 along a line 35. As shown in FIG. 1, foot pedal 20 is locked in a fully-depressed position. However, foot pedal 20 may be actuated using the upper portion of a surgeon's foot to move from a fully undepressed position (not shown) to a fully depressed position as shown in FIG. 1. Foot pedal 20 is used by the surgeon to provide proportional control to certain functions of microsurgical system 10. By way of example, depending on the operating mode of system 10, foot pedal 20 may be used to provide proportional control of vitrectomy probe cut rate, ultrasonic handpiece power, or vacuum level delivered to a handpiece.

Left toe switch 24, right toe switch 26, left heel switch 28, and right heel switch 30 are similarly used by the surgeon to switch between various modes of operation of microsurgical system 10. Left toe switch 24 is preferably a dual mode binary switch. The first mode of switch 24 is actuated when a surgeon presses downward on switch 24 with his or her toe. This first mode is referred to herein as left vertical switch 24a. The second mode of switch 24 is actuated when a surgeon presses in a generally outward, horizontal direction on switch 24 with the side of his or her foot. This second mode is referred to herein as left horizontal switch 24b. Switch 24 is preferably a momentary actuation type switch that provides tactile feedback to the user. Switch 24 is preferably constructed using two Part Number P3-30125 switches available from Otto Controls of Carpenterville, Ill., one for left vertical switch 24a, and a second for left horizontal switch 24b.

Right toe switch 26 is also a dual mode binary switch. The first mode of switch 26 is actuated when a surgeon presses downward on switch 26 with his or her toe. This first mode is referred to herein as right vertical switch 26a. The second mode of switch 26 is actuated when a surgeon presses in a generally outward, horizontal direction on switch 26 with the side of his or her foot. This second mode is referred to herein as right horizontal switch 26b. Switch 26 is preferably a momentary actuation type switch that provides tactile feedback to the user, and is preferably constructed in the same manner as switch 24.

Left heel switch 28 is preferably a binary switch that is actuated when a surgeon presses downward with his or her heel. Right heel switch 30 is a binary switch that is actuated when a surgeon presses downward with his or her heel. Switches 28 and 30 are preferably momentary actuation type switches that provide tactile feedback to the user.

Switches 28 and 30 are each preferably constructed using a Part Number P3-30125 switch available from Otto Controls of Carpenterville, Ill.

Foot controller 10 preferably also has two switch guards 34 and 36. Switch guards 34 and 36 are identical in construction. Each switch guard 34 and 36 preferably has a base member 38 coupled to body 16 and a blade member 40 coupled to base member 38 for guarding one of left toe switch 24 or right toe switch 26. Each of blade members 40 are preferably disposed in a generally parallel, spaced relationship from an outer surface 42 of left toe switch 24 and right toe switch 26. Blade members 40 are spaced a distance 44 from outer surface 42, which is greater than the actuation distance of left horizontal switch 24b and right horizontal switch 26b. In operation, switch guards 34 and 36 thus insure that a surgeon may fully actuate left horizontal switch 24b and right horizontal switch 26b regardless of any nearby obstruction on the operating room floor.

From the above, it may be appreciated that the present invention provides an improved foot controller for a microsurgical system. The present invention is illustrated herein by example, and various modifications may be made by a person of ordinary skill in the art. For example, although the present invention is described hereinabove with switch guards 34 and 36 having a particular geometry, other geometries of foot switch guards are possible as long as such geometries insure full actuation of a horizontal switch movement. As another example, although switches 24 and 26 are described hereinabove as being capable of actuation as a left horizontal switch 24b and a right horizontal switch 26b, such switches may also be actuated in a generally horizontal direction that is not exactly parallel to the operating room floor but is less than vertical actuation (perpendicular to the operating room floor).

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A foot controller for a microsurgical system, comprising:
    a body having a base for supporting said foot controller on a horizontal surface, said base having an exterior vertical surface;
    a switch disposed on said body, said switch having an outer surface positioned proximate said exterior vertical surface of said base, said switch capable of being actuated by a side of a user's foot in a generally horizontal direction away from said body;
    a switch guard coupled to said body and disposed in a spaced relationship to said outer surface of said switch, said switch guard insuring that said switch may be fully actuated in said generally horizontal direction.

2. The foot controller of claim 1 wherein said switch guard is disposed in said spaced relationship at a first distance greater than a second distance that said switch may be activated in said generally horizontal direction.

3. The foot controller of claim 1 wherein said switch guard is disposed in a spaced, generally parallel relationship to said outer surface of said switch.

4. The foot controller of claim 1 wherein said switch guard comprises a base member coupled to said body and a blade member coupled to said base member for insuring that said switch may be fully actuated in said generally horizontal direction.

5. The foot controller of claim 1 wherein
    said generally horizontal direction is a horizontal direction parallel to said horizontal surface.

6. The foot controller of claim 1 wherein said horizontal surface is a floor.

\* \* \* \* \*

UNITED STATES PATENT AND TRADEMARK OFFICE
CERTIFICATE OF CORRECTION

PATENT NO. : 7,626,132 B2 Page 1 of 1
APPLICATION NO. : 11/250093
DATED : December 1, 2009
INVENTOR(S) : Mezhinsky It is certified that error appears in the above-identified patent and that said Letters Patent is hereby corrected as shown below:

On the Title Page,

Item [*] Notice: Subject to any disclaimer, the term of this patent is extended or adjusted under 35 U.S.C. 154(b) by 324 days Delete the phrase "by 324 days" and insert -- by 726 days --

Signed and Sealed this

Tenth Day of August, 2010

David J. Kappos
*Director of the United States Patent and Trademark Office*